(12) United States Patent
Da Silva et al.

(10) Patent No.: US 7,106,043 B1
(45) Date of Patent: Sep. 12, 2006

(54) LOW CAPACITANCE MEASUREMENT PROBE

(75) Inventors: Luiz B. Da Silva, Danville, CA (US); Charles L. Chase, Dublin, CA (US); Bruce W. Haughey, Redwood City, CA (US)

(73) Assignee: BioLuminate, Inc., San Carlos, CA (US)

( * ) Notice: Subject to any disclaimer, the term of this patent is extended or adjusted under 35 U.S.C. 154(b) by 0 days.

(21) Appl. No.: 10/667,118

(22) Filed: Sep. 17, 2003

Related U.S. Application Data

(60) Provisional application No. 60/411,594, filed on Sep. 17, 2002.

(51) Int. Cl.
G01R 31/02 (2006.01)
G01R 27/26 (2006.01)
A61B 8/14 (2006.01)

(52) U.S. Cl. .............. 324/72.5; 324/690; 600/459
(58) Field of Classification Search ............ 324/72.5, 324/72, 437, 445, 446, 449, 538, 715, 724, 324/754, 755, 757, 758, 690, 696, 539, 543, 324/688; 439/63, 322, 429, 482, 551, 578, 439/579, 584, 675; 600/11, 459, 462, 300, 600/587, 591, 595, 547; 606/1, 170; 607/32, 607/41, 45, 48; 73/661, 170.33, 170.34, 73/866.5, 897, 898; 128/897, 898
See application file for complete search history.

(56) References Cited

U.S. PATENT DOCUMENTS

| | | | |
|---|---|---|---|
| 3,665,302 A * | 5/1972 | Lees et al. .................. 324/717 |
| 5,068,619 A * | 11/1991 | Nakano et al. ............. 324/715 |
| 5,325,873 A * | 7/1994 | Hirschi et al. .............. 128/899 |
| 5,342,218 A * | 8/1994 | McMills et al. ............ 439/578 |
| 5,528,155 A * | 6/1996 | King et al. .................. 324/713 |
| 5,800,350 A | 9/1998 | Coppleson et al. ......... 600/372 |
| 5,807,272 A | 9/1998 | Kun et al. ................... 600/547 |
| 6,026,323 A | 2/2000 | Skladnev et al. ........... 600/547 |
| 6,080,149 A * | 6/2000 | Huang et al. ................ 606/32 |
| 6,109,270 A | 8/2000 | Mah et al. .................. 128/920 |
| 6,261,247 B1 * | 7/2001 | Ishikawa et al. ............ 600/587 |
| 6,283,961 B1 * | 9/2001 | Underwood et al. ......... 606/41 |
| 6,531,880 B1 * | 3/2003 | Schneider et al. .......... 324/539 |
| 6,547,788 B1 * | 4/2003 | Maguire et al. ............. 606/41 |
| 6,586,949 B1 * | 7/2003 | Sargent et al. .............. 324/690 |
| 6,645,148 B1 * | 11/2003 | Nguyen-Dinh et al. ..... 600/459 |
| 6,770,027 B1 * | 8/2004 | Banik et al. ................ 600/146 |
| 6,813,515 B1 * | 11/2004 | Hashimshony .............. 600/547 |
| 6,904,307 B1 * | 6/2005 | Karmarkar et al. ......... 600/423 |
| 6,926,669 B1 * | 8/2005 | Stewart et al. .............. 600/439 |

(Continued)

*Primary Examiner*—Anjan Deb
*Assistant Examiner*—Hoai-An D. Nguyen
(74) *Attorney, Agent, or Firm*—Sierra Patent Group, Ltd.

(57) ABSTRACT

A low capacitance measurement probe is disclosed. The low capacitance measurement probe comprises an outer conductor forming an outer wall having an exterior and an interior; a non-conductive spacer forming a first wall having an exterior and an interior with the non-conductive spacer being coupled to the interior of the outer conductor; a conductive layer forming a second wall having an exterior and an interior, the conductive layer coupled to the interior of the first wall; an insulating layer forming a third wall having an exterior and an interior, the insulating layer coupled to the interior of the second wall; and an inner conductor forming an inner wall having an exterior and an interior, the inner conductor coupled to the interior of the third wall. A low capacitance measurement probe system and a method of using a low capacitance measurement probe are also disclosed.

23 Claims, 5 Drawing Sheets

U.S. PATENT DOCUMENTS 6,957,005 B1 * 10/2005 Saulnier et al. ............. 385/137
6,969,354 B1 * 11/2005 Marian ....................... 600/459
6,974,416 B1 * 12/2005 Booker et al. .............. 600/459

* cited by examiner

LOW CAPACITANCE MEASUREMENT PROBE

PRIORITY CLAIM

This application claims priority to U.S. Provisional Application Ser. No. 60/411,594, filed on Sep. 17, 2002.

BACKGROUND

Various methods and devices have been developed to measure the electrical properties of tissue in an effort to distinguish between cancerous and non-cancerous tissue. For example, U.S. Pat. No. 5,800,350 to Coppleson et al. discloses an apparatus for tissue type recognition. In particular, an apparatus includes a probe configured to contact the tissue and subject the tissue to a plurality of different stimuli such as electrical, light, heat, sound, magnetic and to detect plural physical responses to the stimuli. The apparatus also includes a processor that processes the responses in combination in order to categorize the tissue. The processing occurs in real-time with an indication of the tissue type (e.g. normal, pre-cancerous/cancerous, or unknown) being provided to an operator of the apparatus.

The complex impedance of tissue is generally measured by applying a voltage across at least two electrodes and measuring the current that flows between the electrodes. In order to make accurate measurements these devices employ multiple electrodes (U.S. Pat. No. 5,807,272, U.S. Pat. No. 6,026,323).

These devices are generally large and/or require multiple needles to be inserted into the tissue. In addition, to improve the accuracy of these diagnostic devices multiple sensors are integrated into the probe. For example, U.S. Pat. No. 6,109,270 to Mah et. al. and pending U.S. patent application Ser. No. 09/947,171 to Hular et al. disclose a multimodality instrument for tissue characterization. In order to minimize trauma, what is needed in the art is a new small electrical probe device that provides accurate measurements of the tissue impedance and provides space for additional sensors.

SUMMARY

A method and apparatus for measuring the electrical impedance of tissue over a wide frequency range is disclosed. A signal generator drives a current through the tissue that is measured along with the voltage to determine the tissue impedance. A low capacitance probe allows accurate measurements to be made using a small device that can easily penetrate tissue. The measurements can be analyzed to determine tissue type or state.

The present invention is a method and a system that can be used by physicians to accurately measure the electrical impedance of tissue over a wide frequency range. The disclosed system can be used by surgeons to determine whether a suspicious lesion is cancer or normal tissue. In normal use, the present invention can be used by a physician to measure tissue electrical properties. The physician inserts the probe into tissue and the response of the tissue to electrical energy is determined. The measurements made with the probe are then analyzed by the electronic system to determine tissue type or state. In a preferred embodiment, the system is used to diagnose cancer.

A low capacitance measurement probe is disclosed. The low capacitance measurement probe comprises an outer conductor forming an outer wall having an exterior and an interior; a non-conductive spacer forming a first wall having an exterior and an interior with the non-conductive spacer being coupled to the interior of the outer conductor; a conductive layer forming a second wall having an exterior and an interior, the conductive layer coupled to the interior of the first wall; an insulating layer forming a third wall having an exterior and an interior, the insulating layer coupled to the interior of the second wall; and an inner conductor forming an inner wall having an exterior and an interior, the inner conductor coupled to the interior of the third wall.

A low capacitance measurement probe system is also disclosed. The low capacitance measurement probe system comprises a low capacitance measurement probe and control electronics electrically coupled to the low capacitance measurement probe. The control electronics has a display. The low capacitance measurement probe comprises an outer conductor forming an outer wall having an exterior and an interior; a non-conductive spacer forming a first wall having an exterior and an interior with the non-conductive spacer being coupled to the interior of the outer conductor; a conductive layer forming a second wall having an exterior and an interior, the conductive layer coupled to the interior of the first wall; an insulating layer forming a third wall having an exterior and an interior, the insulating layer coupled to the interior of the second wall; and an inner conductor forming an inner wall having an exterior and an interior, the inner conductor coupled to the interior of the third wall.

A method for collecting measurements using a low capacitance measurement probe system. The method comprises disposing a low capacitance measurement probe in a designated area, directing an electrical current to the low capacitance measurement probe from control electronics, measuring electrical impedance between an inner conductor and an outer conductor of the low capacitance measurement probe to collect a first measurement, and directing the first measurement to the control electronics.

BRIEF DESCRIPTION OF THE DRAWINGS

Referring now to the figures, wherein like elements are numbered alike.

DETAILED DESCRIPTION

Those of ordinary skill in the art will realize that the following description is illustrative only and not in any way limiting. Other embodiments will readily suggest themselves to such skilled persons.

The present invention provides a system that can be used by physicians to accurately measure the electrical impedance of tissue over a wide frequency range.

Figure 1:
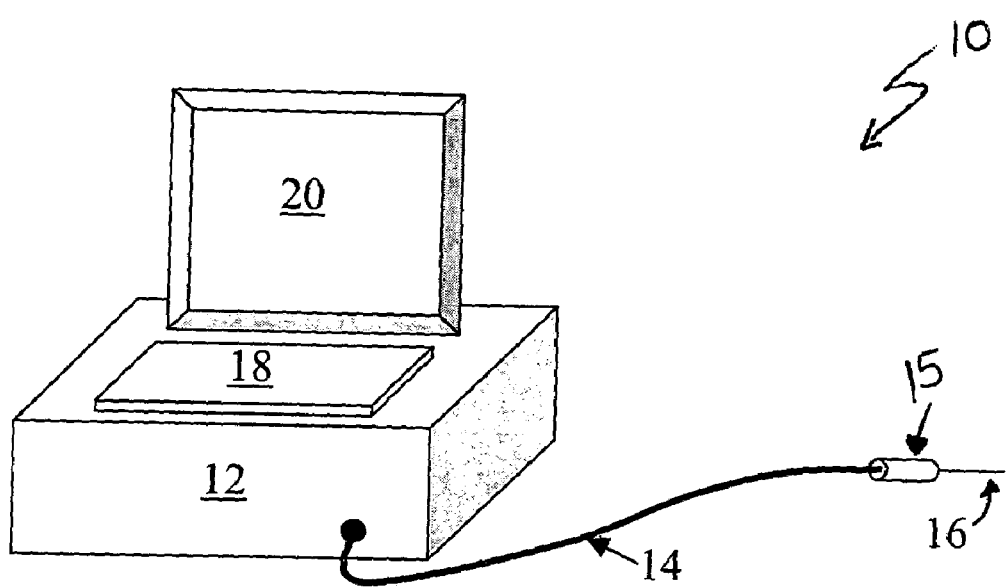
FIG. 1 illustrates the key components of a low capacitance tissue probe system.

FIG. 1 illustrates the major components of the low capacitance tissue probe measurement system 10. A control electronics module 12 is connected to the low capacitance probe 16 via a cable 14.

The probe 16 has a handle 15 for ease in using the probe 16. The handle 15 can be made from any suitable material that allows for a tactile feel. Suitable materials include plastic, polystyrene, polycarbonate, and the like.

The control electronics can be disposed in the control electronics module, as illustrated, or in the handle 15 of the probe 16. The control electronics consists of a signal generator and a signal detector. The control electronics are also equipped with devices for maintaining safety. Signals are directed through cables (e.g., cable 14), with shielded cables such as coaxial cables, shielded twisted pair, and the like preferred.

In normal use, the control electronics receives the data from the low capacitance probe 16 and processes the data for display on the monitor (or screen) 20. In a preferred embodiment, the data can be displayed directly on the probe 16. A user interface 18 is used by the user to control data acquisition, data displayed and analysis. The user interface can be a keyboard, a touch pad, a touch screen, buttons, a mouse, and the like. In normal use, the distal tip (or probe end or sensing end) 34 of the probe 16 is touched against or disposed proximate the tissue sample for measurement. In an alternative embodiment, the distal tip 34 of the probe 16 is shaped to penetrate into tissue sample to collect multiple measurements along the probe trajectory. The probe 16 is preferably round in shape in order to penetrate through tissue, although other suitable shapes are contemplated.

Figure 2:
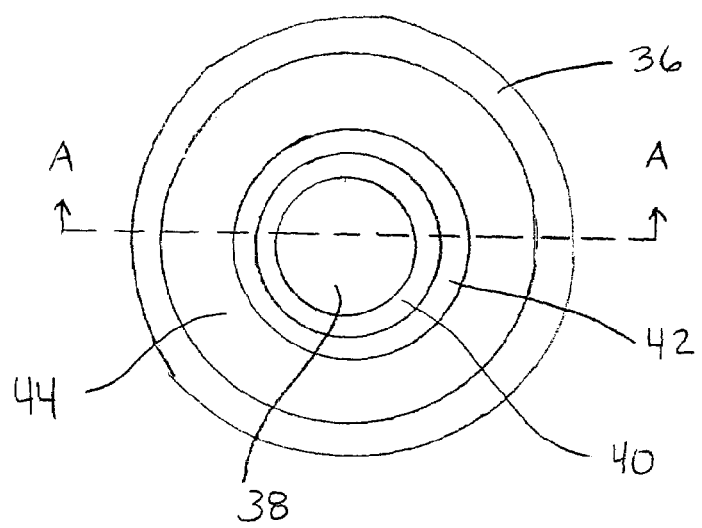
FIG. 2 is a cross-sectional end view of the distal tip of a probe.

FIG. 2 illustrates a cross-sectional end view of the distal tip 34 of the probe 16. The probe 16 consists of an outer conductive sheath (or outer electrode or outer conductor) 36 that acts as one electrode for the probe 16. The central electrode (or central conductor or inner electrode or inner conductor) 38 is also made of a conductive material. The electrodes can be comprised of a conductive material such as stainless steel, platinum, gold, conductive plastic, silver, copper, and the like. The central electrode 38 is coated with an insulating layer 40. The insulating layer 40 can be any biocompatible nonconductive polymer such as polyethylene, polyurethane, polytetrafluoroethylene an example is TEFLON®, polyimide, parylene, glass, ceramic, silicone, epoxy, and the like. A conductive layer (or thin shield layer) 42 acts to shield the central conductor 38 and reduce the effective capacitance of the spacer area (or non-conductive spacer or non-conductive material or fiber optics) 44. The conductive layer 42 can be comprised of a conductive material such as stainless steel, platinum, gold, conductive plastic, silver, copper, and the like. The spacer area 44 can be any biocompatible nonconductive polymer such as polyethylene, polyurethane, polytetrafluoroethylene an example is TEFLON®, polyimide, parylene, glass, ceramic, silicone, epoxy, fiber optics with epoxy fill, and the like.

Figure 3:
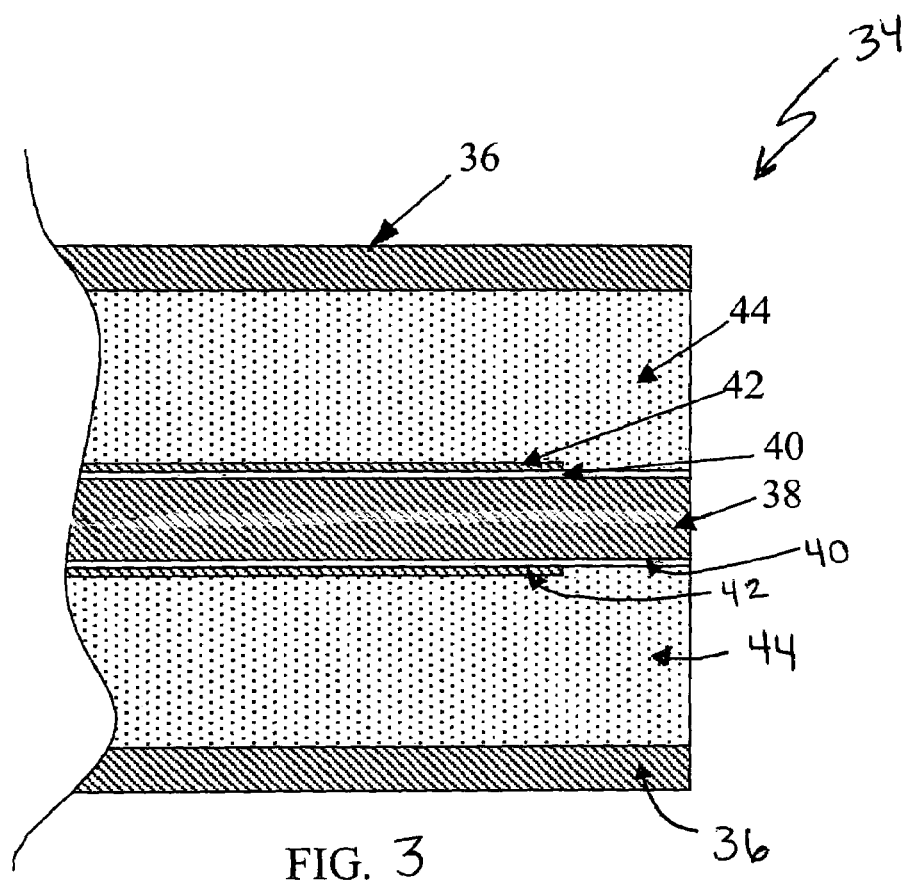
FIG. 3 is a cross-sectional view of a first embodiment of a distal tip of a probe.

FIG. 3 illustrates a cross-sectional view along lines A—A of the distal tip 34 of one embodiment of the probe 16. The probe 16 consists of an outer conductive sheath 36 that acts as one electrode for the probe 16. The central electrode 38 is coated with an insulating layer 40. A conductive layer 42 acts to shield the central conductor 38 and reduce the effective capacitance of the spacer area 44.

Figure 4:
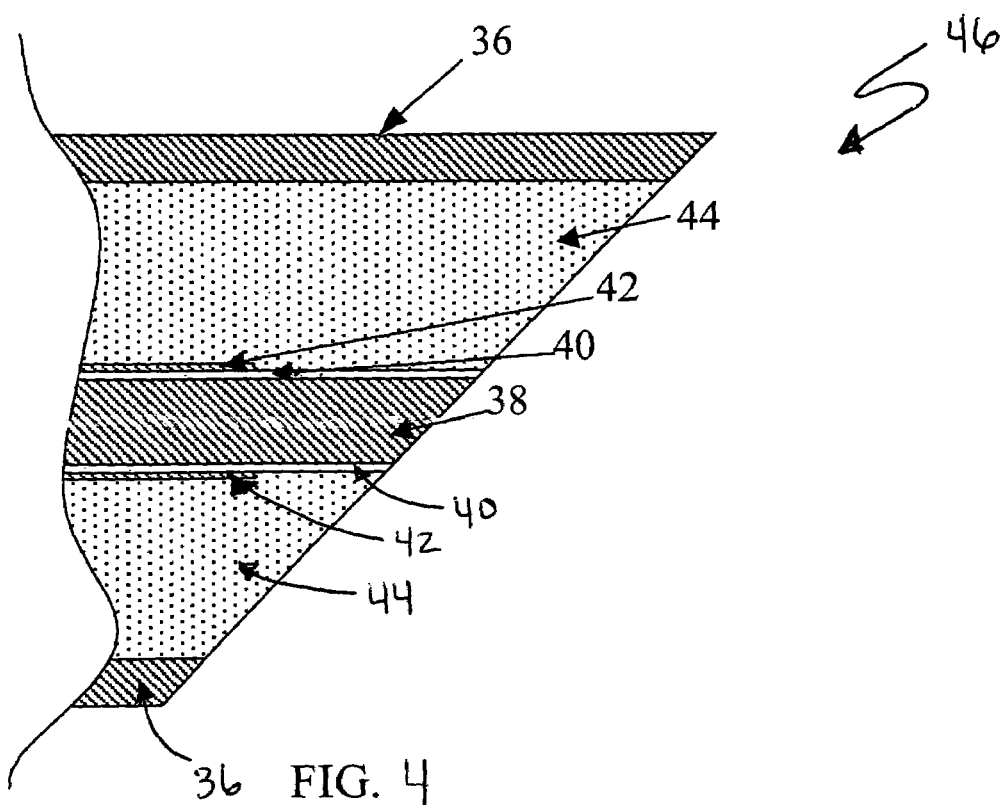
FIG. 4 is a cross-sectional view of a second embodiment of a distal tip of a needle-like probe.

FIG. 4 illustrates a cross-sectional view along lines A—A of an alternative distal tip 46 of another embodiment of a needle-like version of probe 16 that is sharpened to a point in order to easily penetrate tissue. The probe 16 consists of an outer conductive sheath 36 that acts as one electrode for the probe 16. The central electrode 38 is coated with an insulating layer 40. A conductive layer 42 acts to shield the central conductor 38 and reduce the effective capacitance of the spacer area 44.

Figure 5:
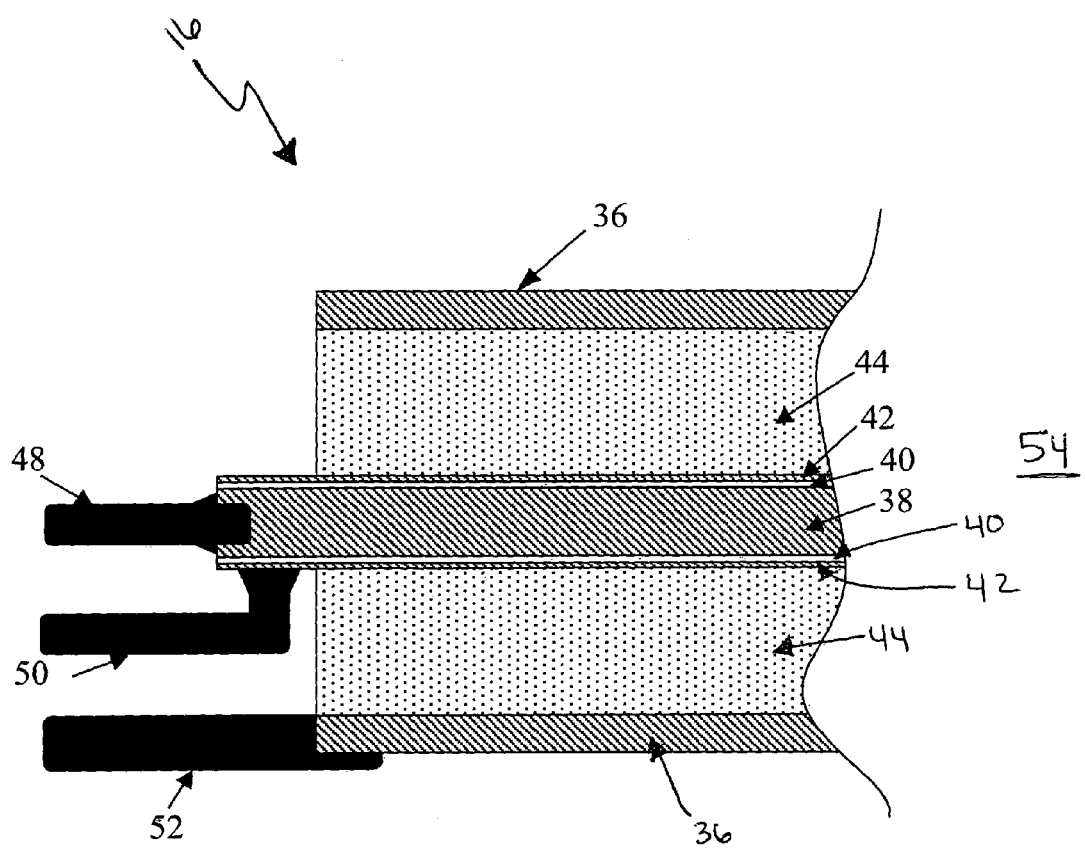
FIG. 5 is a cross-sectional view of the electrical connections to the proximal end of the probe.

FIG. 5 illustrates a cross-sectional view of the electrical connections with the probe 16 with the distal end of the probe being in the tissue 54. The control module 12 generates a voltage on electrical wire 48 relative to wire 52. The control module 12 also buffers and drives the same voltage to wire 50 relative to wire 52, thereby effectively neutralizing the parasitic capacitance seen by the center electrode 38 for all but the short distance (e.g., about 0.1 millimeters to about 3 millimeters) of its length not covered by the shield 42 at the distal end which contacts the tissue being measured. Tissue electrical impedance properties are determined by measuring the electrical current flowing between wires 48 and 52 relative to the voltage applied to between wires 48 and 52. Neutralizing the parasitic capacitance of the probe electrode is critical to obtaining accurate tissue electrical impedance properties at high frequencies (e.g., greater than about 2 khz) where the probe capacitance would otherwise dominate the measurement. The voltage applied between electrodes 38 and 36 are typically less than about 3 volts peak-to-peak, and the current flowing through tissue 54 is limited to about 100 microamps, or less, to minimize potential adverse affects on tissue 54. The applied voltage is typically a sine-wave applied at one or more frequencies of interest. An alternate method can be applying a square wave or pulse and analyzing the frequency components on the leading and/or trailing edge of the waveform.

The multilayered electrode design reduces probe capacitance. The needle-like probe uses an outer conductor as one electrode and a central conductor as the other electrode. In order to allow for additional sensors to be integrated into the probe, a non-conductive material fills the area between the outer electrode and central electrode. In order to reduce the capacitance in the measurement circuit, the central conductor has a thin insulating layer and a thin conductive layer. The thin conductive layer and the central conductor are kept at the same voltage during the measurement.

Figure 6:
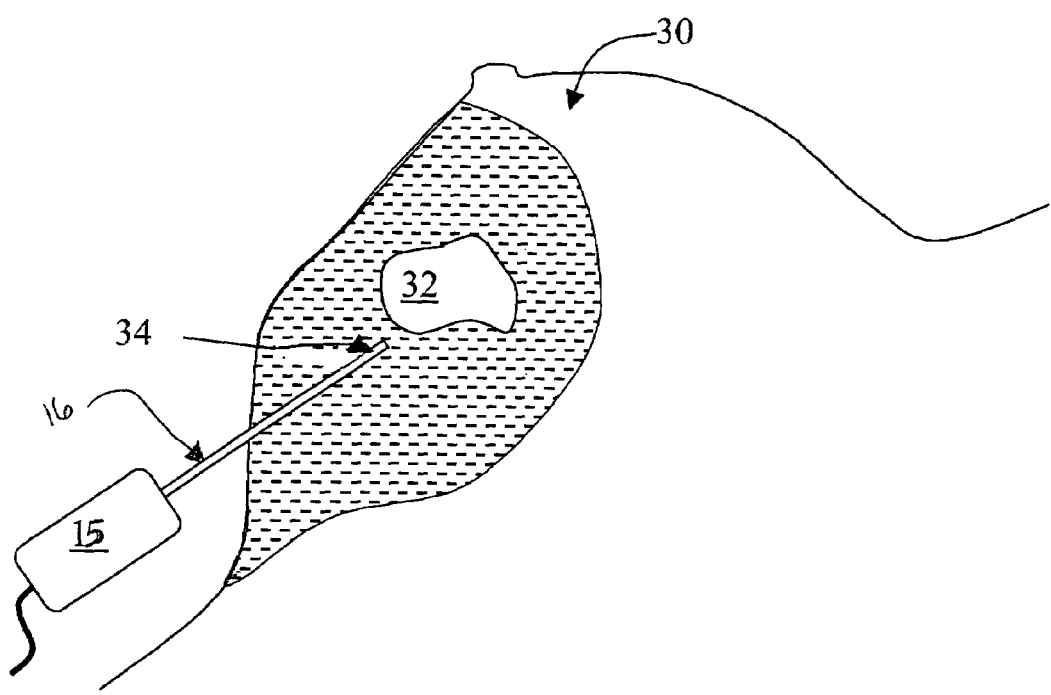
FIG. 6 illustrates a probe utilized in the diagnosis of breast cancer.

FIG. 6 illustrates the insertion of the probe 16 into a breast 30 (or any other appropriate part of the body) to collect measurements for the diagnosis of a suspicious lesion (tissue mass or desired target area) 32. Tissue properties (e.g., electrical impedance) are measured at the distal tip 34 of the probe 16 and the measurements are sent to the control electronics 12 for display on the monitor 20. The measurements are stored in a database for comparison to other measurements to determine whether the tissue is cancerous.

The following describes a preferred method, although other sequences of the following method can be utilized, of using the low capacitance measurement probe and system:

1. The user turns the system power on.
2. The user attaches the sterile probe assembly consisting of items 14, 15, and 16 to item 12.
3. The system alerts the user when it is acceptable to start the procedure.
4. The user inserts the sterile probe 16 tip into the breast (or other appropriate tissue) directing the probe tip into and possibly through the suspicious lesion, preferably at a rate of about 1 centimeter per second or less. (The system will automatically detect when the probe tip first touches the breast, or the user could alternatively manually start the data acquisition by pressing a key, or button, or icon on the touch screen.)
5. The user may make several passes through the suspicious lesion.
6. Several methods of presenting the result are possible including:
    a. Analyzing and displaying the type of tissue the probe contacts in real time.

b. Analyzing and displaying the tissue types encountered at the end of the probing procedure.

7. Possible indicators of the result include: "benign", "malignant", "unknown", and a confidence indicator such as "tissue is benign. Confidence factor=98%".

8. After the procedure is complete, the probe assembly will be disposed, or re-sterilized for subsequent use.

In normal use, the control electronics generate an electrical signal, which is a voltage, and applies the electrical signal across the center electrode and the outer electrode (to create a voltage potential). The control electronics then applies the same electrical voltage potential to the shield 42 and the module measures the resulting current flowing between the electrodes 38 and 36. The control electronics module maintains safety limits for current running through the tissue.

In general, a sinusoidal voltage is applied to the tissue over a wide frequency range. A suitable frequency range for identifying cancer is about 2 kHz to about 10 MHz. The impedance is calculated by dividing the applied voltage by the resultant current flowing between electrodes 38 and 36. The complex impedance is determined by measuring both the phase angle and amplitude.

Driving the shield 42 at the same electrical potential as central electrode 38 relative to outer electrode 36 while measuring the current flow through the central electrode 38 eliminates the relatively large parasitic capacitance between the central electrode 38 and the outer electrode 36. Since this parasitic capacitance represents the majority of the probe capacitance, a more accurate measurement of the tissue properties is obtained.

A variety of numerical analysis techniques can be used to determine tissue type and state from the complex impedance. In most cases, analysis requires a database of measured impedance properties for known tissue types. This database is then used as a basis for pattern recognition algorithms. Neural network algorithms, cluster analysis, and other multivariate data analysis techniques could also be used to determine tissue type or state.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A low capacitance measurement probe comprising:
    a proximate end and a distal end of said probe;
    a tip on said distal end of said probe for injecting said probe into tissue;
    an outer conductor forming an outer wall having an exterior and an interior;
    a non-conductive spacer forming a first wall having an exterior and an interior, said non-conductive spacer coupled to said interior of said outer conductor;
    a conductive layer forming a second wall having an exterior and an interior, said conductive layer coupled to said interior of said first wall;
    an insulating layer forming a third wall having an exterior and an interior, said insulating layer coupled to said interior of said second wall; and
    an inner conductor forming an inner wall having an exterior and an interior, said inner conductor coupled to said interior of said third wall.

2. The low capacitance measurement probe of claim 1, wherein an electrical circuit is created when said outer conductor and said inner conductor electrically communicate responsive to contact with tissue.

3. The low capacitance measurement probe of claim 1, further comprising wires coupled to said outer conductor, said conductive layer, and said inner conductor.

4. The low capacitance measurement probe of claim 1, wherein the low capacitance measurement probe has a probe end and a control end.

5. The low capacitance measurement probe of claim 4, further comprising a handle coupled to said control end.

6. The low capacitance measurement probe of claim 4, further comprising:
    control electronics configured to send electrical signals to the low capacitance measurement probe and configured to receive measurements for indication on a display, said control electronics disposed in said handle.

7. The low capacitance measurement probe of claim 6, further comprising:
    a user interface coupled to said control electronics.

8. The low capacitance measurement probe of claim 1, further comprising:
    a control electronics module configured to send electrical signals to the low capacitance measurement probe and configured to receive measurements for indication on a display.

9. The low capacitance measurement probe of claim 8, further comprising:
    a user interface coupled to said control electronics.

10. The low capacitance measurement probe of claim 1, wherein said outer conductor, said inner conductor, and said conductive layer are comprised of a material selected from the group consisting of stainless steel, platinum, gold, silver, copper, and conductive plastic.

11. The low capacitance measurement probe of claim 1, wherein said non-conductive spacer and said insulating layer are selected from the group consisting of polyethylene, polyurethane, polytetrafluoroethylene, polyimide, parylene, glass, epoxy, ceramic, and silicone.

12. A low capacitance measurement probe system comprising:
    a low capacitance measurement probe having a tip on a distal end for injecting said probe into tissue comprising:
        an outer conductor forming an outer wall having an exterior and an interior;
        a non-conductive spacer forming a first wall having an exterior and an interior, said non-conductive spacer coupled to said interior of said outer conductor;
        a conductive layer forming a second wall having an exterior and an interior, said conductive layer coupled to said interior of said first wall;
        an insulating layer forming a third wall having an exterior and an interior, said insulating layer coupled to said interior of said second wall; and
        an inner conductor forming an inner wall having an exterior and an interior, said inner conductor coupled to said interior of said third wall; and
    control electronics electrically coupled to said low capacitance measurement probe, said control electronics having a display.

13. The system of claim 12, wherein an electrical circuit is created when said outer conductor and said inner conductor electrically communicate responsive to contact with tissue.

14. The system of claim 12, further comprising wires coupled to said outer conductor, said conductive layer, and said inner conductor.

15. The system of claim 12, wherein said low capacitance measurement probe has a probe end and a control end.

16. The system of claim 15, further comprising a handle coupled to said control end.

17. The system of claim 16, wherein said control electronics are disposed in said handle.

18. The system of claim 12, wherein said low capacitance measurement probe is configured to send electrical signals to said control electronics.

19. The system of claim 12, wherein said control electronics are disposed in a module.

20. The system of claim 12, wherein said control electronics is configured to receive measurements and configured to indicate said measurements on said display.

21. The system of claim 12, wherein said outer conductor, said inner conductor, and said conductive layer are comprised of a material selected from the group consisting of stainless steel, platinum, gold, silver, copper, and conductive plastic.

22. The system of claim 12, wherein said non-conductive spacer and said insulating layer are selected from the group consisting of polyethylene, polyurethane, polytetrafluoroethylene, polyimide, parylene, glass, ceramic, epoxy, and silicone.

23. The system of claim 12, further comprising:

a user interface coupled to said control electronics.

* * * * *